US00RE43525E

(19) United States
(12) Reissued Patent
Landi

(10) Patent Number: US RE43,525 E
(45) Date of Reissued Patent: Jul. 17, 2012

(54) ATHLETIC PROTECTOR CUP

(75) Inventor: James J. Landi, Maplewood, NJ (US)

(73) Assignee: XO Athletic, Co., Union, NJ (US)

(21) Appl. No.: 10/384,309

(22) Filed: Mar. 6, 2003

Related U.S. Patent Documents

Reissue of:
(64) Patent No.: 6,319,219
Issued: Nov. 20, 2001
Appl. No.: 09/653,910
Filed: Sep. 1, 2000

(51) Int. Cl.
*A61F 13/00* (2006.01)
(52) U.S. Cl. ..... 602/67; 602/68; 128/846
(58) Field of Classification Search ..... 602/67–73; 128/845–846, 891, 95.1, 96.1, 98.1, 105.1; 2/425
See application file for complete search history.

(56) References Cited

U.S. PATENT DOCUMENTS

| | | | | |
|---|---|---|---|---|
| 1,972,275 A | | 9/1934 | Record | |
| 2,283,684 A | | 5/1942 | Matthews | |
| 3,176,686 A | * | 4/1965 | Barnes | 128/846 |
| 3,782,375 A | | 1/1974 | Donars | |
| 3,873,998 A | | 4/1975 | Norris et al. | |
| 4,134,400 A | | 1/1979 | DiMatteo | |
| 4,257,414 A | | 3/1981 | Gamm et al. | |
| 4,453,541 A | | 6/1984 | Castelli et al. | |
| 4,471,772 A | | 9/1984 | Miller, Jr. | |
| 4,922,899 A | | 5/1990 | Graff et al. | |
| 4,989,594 A | | 2/1991 | Doherty et al. | |
| 5,174,307 A | | 12/1992 | Thompson | |
| 5,479,942 A | * | 1/1996 | DiMatteo | 128/846 |
| 5,722,093 A | | 3/1998 | Andresen | |
| 6,048,327 A | | 4/2000 | Kieffer | |

OTHER PUBLICATIONS

Fundamentals and Material Development for Thermoplastic Elastomer (TPE) Overmolding Journal of Injection Molding Technology, Mar. 2000, vol. 4, No. 1.

* cited by examiner

*Primary Examiner* — Michael A. Brown
(74) *Attorney, Agent, or Firm* — Lerner, David, Littenberg, Krumholz & Mentlik, LLP

(57) ABSTRACT

An athletic protector cup is provided including a rigid cup-shaped base member and an impact resistant resilient body which is fixedly attached to an exterior surface and around a periphery of the base member. The resilient body includes a flange extending beyond portions of the base member edge and having a geometry for providing additional impact resistance.

41 Claims, 8 Drawing Sheets

ATHLETIC PROTECTOR CUP

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates generally to athletic protector cups, and more particularly to an athletic protector cup having a flexible resilient portion molded thereto for providing improved protection and comfort to the wearer.

2. Description of the Prior Art

Devices for the protection of the male groin region are extensively utilized in athletics. In athletic competition, particularly body contact sports such as football, baseball, hockey, soccer and the like, protective devices are worn by the players to avoid injury due to inadvertent blows to the groin area. The most common protective device includes a cup supported by a jockstrap. Protector cups of this character are usually formed from a plastic material, such as polypropylene or polyethylene, which is sufficiently rigid to retain its shape even when struck a relatively severe blow.

Historically, protector cups have been provided with a resilient padding about their periphery both for the comfort of the wearer and, in some measure, to absorb the impact of a blow to the protector cup. The resilient padding is usually formed from a soft, flexible foam-like material, such as foam rubber or polyurethane foam, and is usually provided in the form of a limited elongated strip manually attached to the peripheral edge of the cup with the aid of an adhesive. Such conventional padded cups suffer a number of disadvantages and limitations. For instance, the pad attachment procedure is both time consuming and costly, and the bond between the padding and the protector cup is often deficient. Separation of the padding and the protector cup typically occurs during repeated use of the protector when the padding is peeling away from the restricted area of attachment to the cup. Furthermore, such known structures, in view of the restricted extent of the padding, offer only limited impact absorption protection. Consequently, upon impact a significant portion of the blow is transferred to the body of the wearer. Examples of athletic protector cups incorporating such conventional peripheral padding are provided in U.S. Pat. Nos. 2,283,684; 3,782,375; 4,453,541 and 4,134,400.

U.S. Pat. No. 4,257,414 discloses an athletic protector cup having a resilient peripheral binding molded to a peripheral cup flange. The molded binding structure disclosed in the this patent provides some benefits vis-a-vis the aforementioned conventional padded cup structures. For instance, molding provides a more efficient and cost-effective means of attachment than a conventional adhesive foam strip. Furthermore, the disclosed binding is contoured to have a relatively thick outwardly-extending body portion for providing improved comfort to the wearer and improved impact absorption. However, the athletic cup structure disclosed in this patent has some significant drawbacks and limitations. For instance, to prevent separation of the molded binding from the cup over time, the cup must be manufactured having a series of perforations along the flange. In other words, to achieve adequate attachment of the binding to the cup flange, the binding material is required to flow through relatively small perforations during assembly. This is necessary to provide interlocks integrally connecting the portions of the binding lying on opposite sides of the flange. Furthermore, the relative increase in impact resistance provided by the disclosed flange geometry leaves significant room for improvement. This is because only a limited area of hard-shell is covered by soft binding. Additionally, the disclosed binding surface geometry of the outwardly extending body portion includes sharp edges which could result in chafing during frictional contact with the wearer's body.

Accordingly, there is an established need for an athletic protector cup overcoming the aforementioned drawbacks and limitations of the prior art.

SUMMARY OF THE INVENTION

It is an object of the present invention to provide an athletic protector cup including a rigid plastic base having a resilient body extending over a substantial portion or entire outer surface thereof for dampening the impact of a blow to the outer surface of the cup.

It is another object of the present invention to provide an athletic protector cup having a peripheral flexible flange for further dampening the impact of a blow to the outer surface of the cup.

It is a further object of the present invention to provide an athletic protector cup having a peripheral flexible flange geometry designed to collapse under forces applied by the cup to the wearer during various body movements, or under the force of a sudden impact, in such a manner as to create a cushioning barrier between the rigid plastic base and the wearer's body.

It is still a further object of the present invention to provide an athletic protector cup having a flexible flange incorporating a surface geometry for providing improved comfort to the wearer by minimizing frictional contact with the wearer's skin.

It is yet a further object of the present invention to provide an athletic protector cup incorporating a flexible resilient body portion molded to a rigid base in such manner as to minimize the risk of separation of the molded portion from the rigid base.

One aspect of the invention provides an athletic protector including a rigid cup-shaped member having interior and exterior surfaces defined along their peripheries by an edge having an upper segment and opposite side segments. A flexible resilient body covers a substantial portion of the exterior surface and extends around at least a portion of the peripheral edge. The resilient body is fixedly attached over at least a portion of the exterior surface of the base member.

As to another aspect of the invention, the flexible resilient body is molded over substantially the entire exterior surface of the rigid cup base member and around the length of peripheral edge. The flexible resilient body can also be molded over substantially the entire interior and exterior surface of the rigid cup-shaped base member.

A further embodiment of the invention provides an athletic protector wherein the upper segment of the peripheral edge terminates at a first integral lip and the lower segment of the peripheral edge terminates at a second integral lip. The flexible resilient body envelopes the first and second integral lips. The opposite side segments of the rigid cup peripheral edge have an inwardly stepped surface forming an exterior leading edge. The flexible resilient body is molded around the leading edge.

Still another aspect of the invention provides the flexible resilient body having a cup-shaped portion overlying substantially the entire exterior surface of the rigid cup-shaped base member. The cup-shaped portion of the flexible-resilient body has a thickened flange portion extending around substantially its entire periphery. The thickened flanges portion terminates at a rounded end having generally crescent-shaped cross-section geometry. The rounded end has a convex outer surface and a concave inner surface. Upon application of a force to an exterior surface of the athletic protector, the thickened flange portion collapses inwardly in such a manner as to form a cushion barrier between the rigid peripheral edge of the base member and the body of the wearer.

Still further aspect of the invention provides the athletic protector in which the resilient flexible body is made of an elastomer and the resilient flexible body is injection molded to the rigid cup-shaped base.

These and other objects and aspects of the invention are achieved by the athletic protector cup which is described hereinbelow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION OF THE PREFERRED EMBODIMENTS

The athletic protector cup of the present invention comprises a rigid unified structure and a resilient structure. When the athletic protector cup is fully constructed these elements are integrated to form a single cup structure. However, for the purpose of clarity, in portions of the following description and referenced drawing figures the respective structures are described and illustrated isolated from each other.

Referring initially to FIGS. 1-6, wherein the rigid portion of the cup structure, shown generally at 10, is illustrated in detail. The cup-shaped rigid base member 10 is contoured to cover and protect the genitals of a wearer and can be formed from numerous rigid plastic materials, such as polypropylene or high-density polyethylene. The rigid cup base has arcuate exterior and interior surfaces, 16 and 18, respectively. Furthermore, the rigid cup base has upper and lower ends, shown generally at 14 and 12, respectively. Although the exterior and interior surfaces can be smooth, in the embodiment of the invention illustrated in FIGS. 1-6, the upper 14 and lower 12 cup ends, have respective integral lip portions, 22 and 20, extending outwardly therefrom. The lips are thickest in cross section at their respective midpoints, each having an inwardly tapering smooth surface curving along the body perimeter in a direction away from its midpoint.

Figures 1, 2, 3:
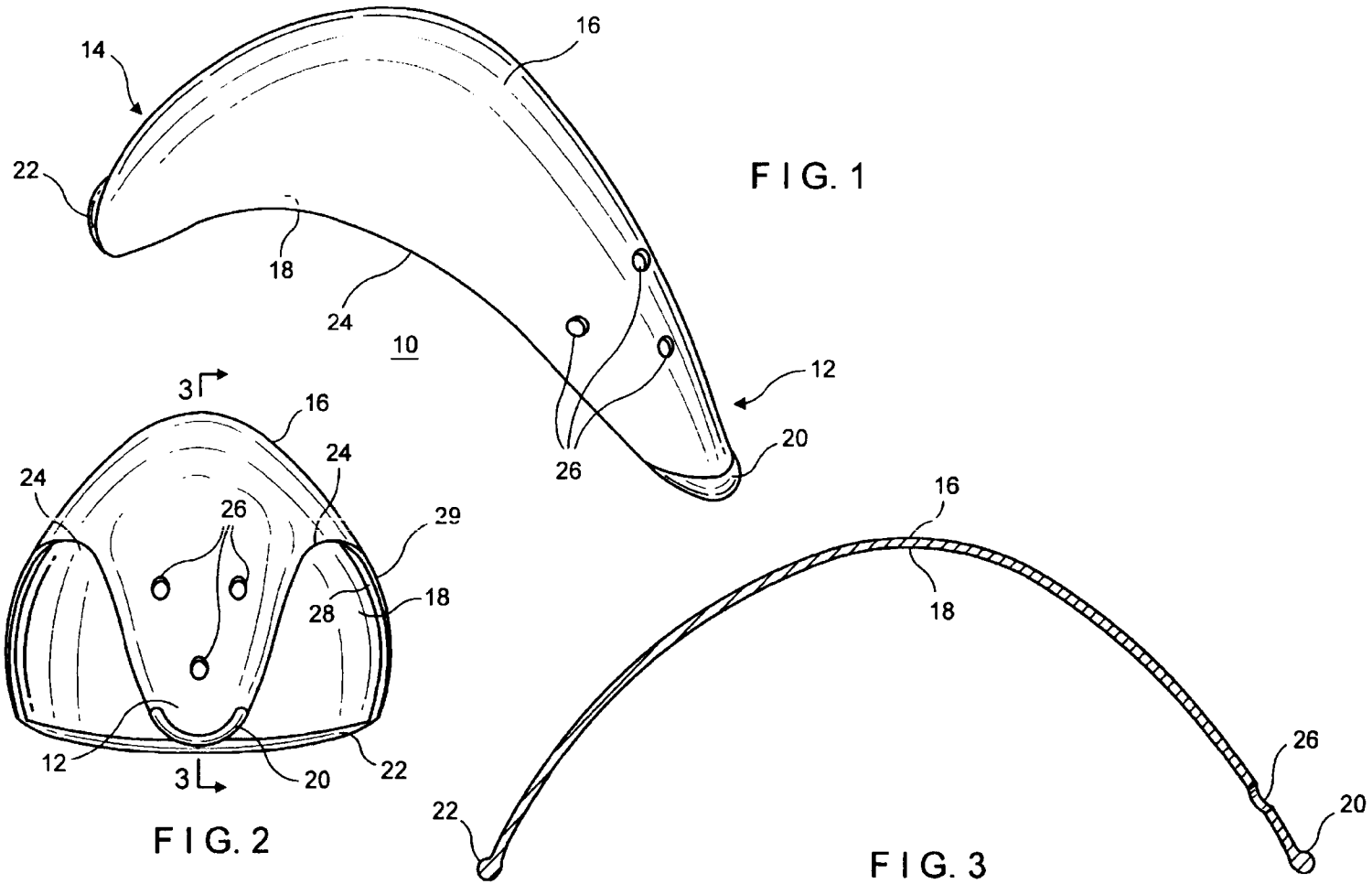
FIG. 1 is a perspective view of a rigid cup-shaped body portion of an athletic protector cup in accordance with the present invention.
FIG. 2 is a front elevational view of the rigid cup-shaped body of FIG. 1, viewed from lower end 12.
FIG. 3 is a cross-sectional view according to section line 3-3 of FIG. 2.
Figure 4:
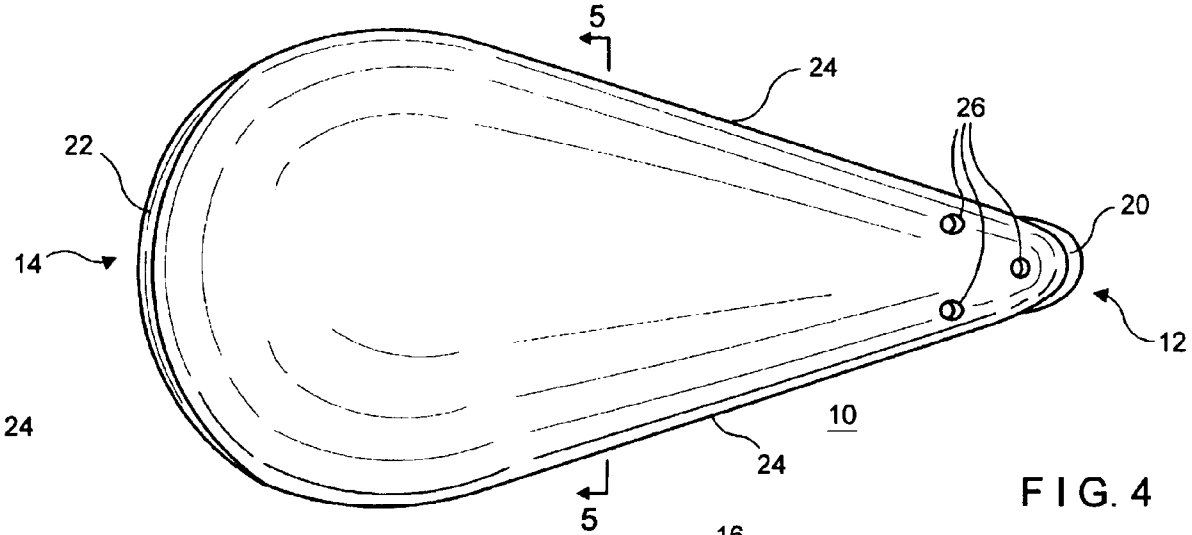
FIG. 4 is a top plan view of the rigid-cup shaped body depicted in FIG. 1.
Figure 6:
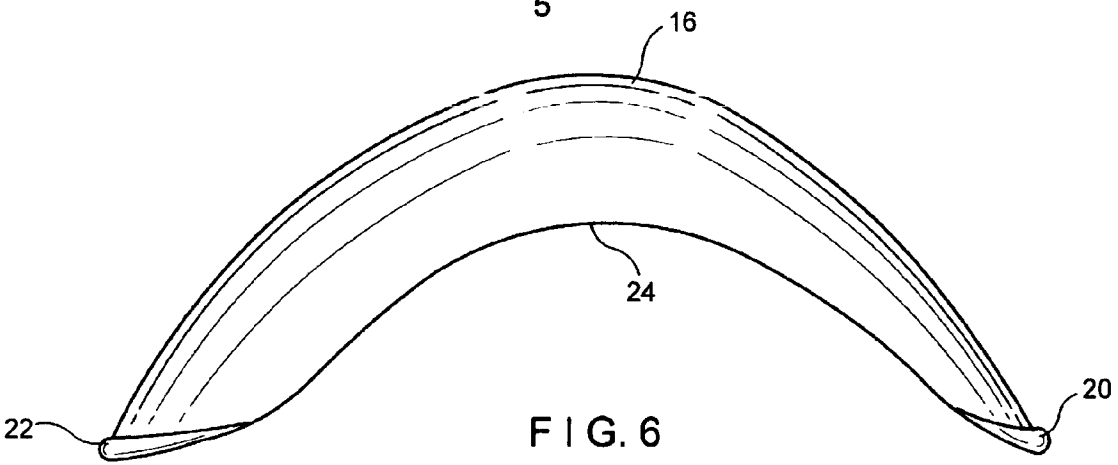
FIG. 6 is a side view elevational of the rigid cup-shaped body depicted in FIG. 1.
Figure 5:
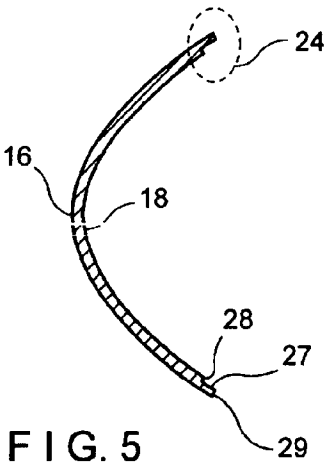
FIG. 5 is a cross-sectional view according to section line 5-5 of FIG. 4.
Figure 7:
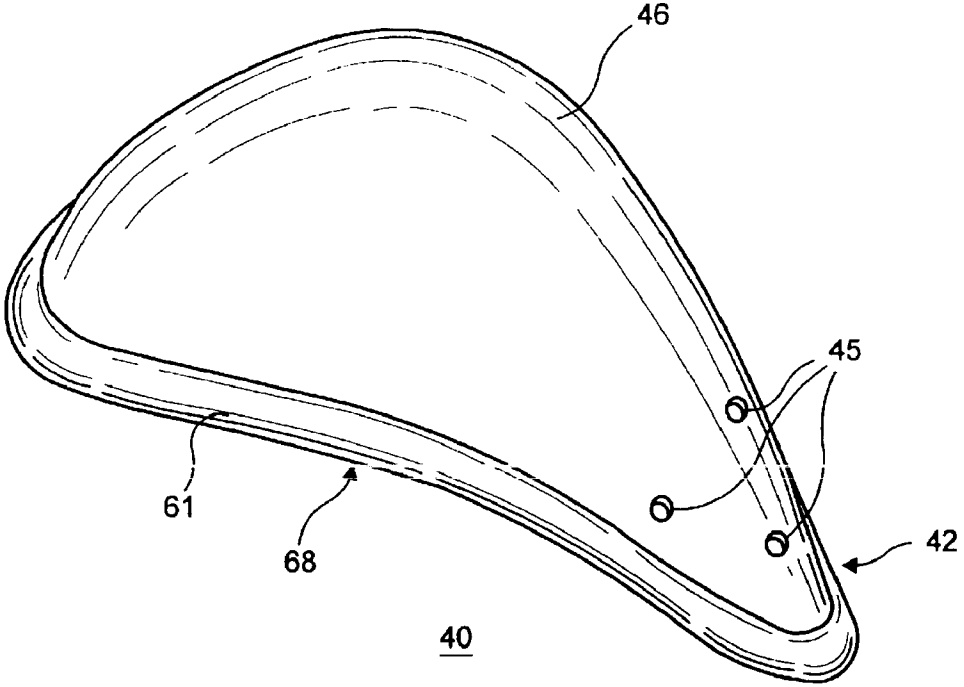
FIG. 7 is a perspective view of a resilient body portion of an athletic protector cup in accordance with the present invention.
Figure 9:
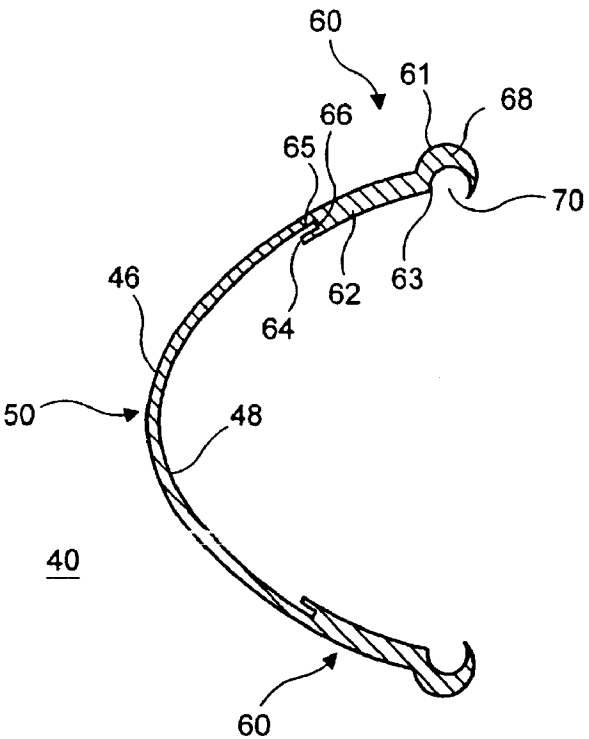
FIG. 9 is a cross-sectional view according to section line 9-9 of FIG. 8.
Figure 8:
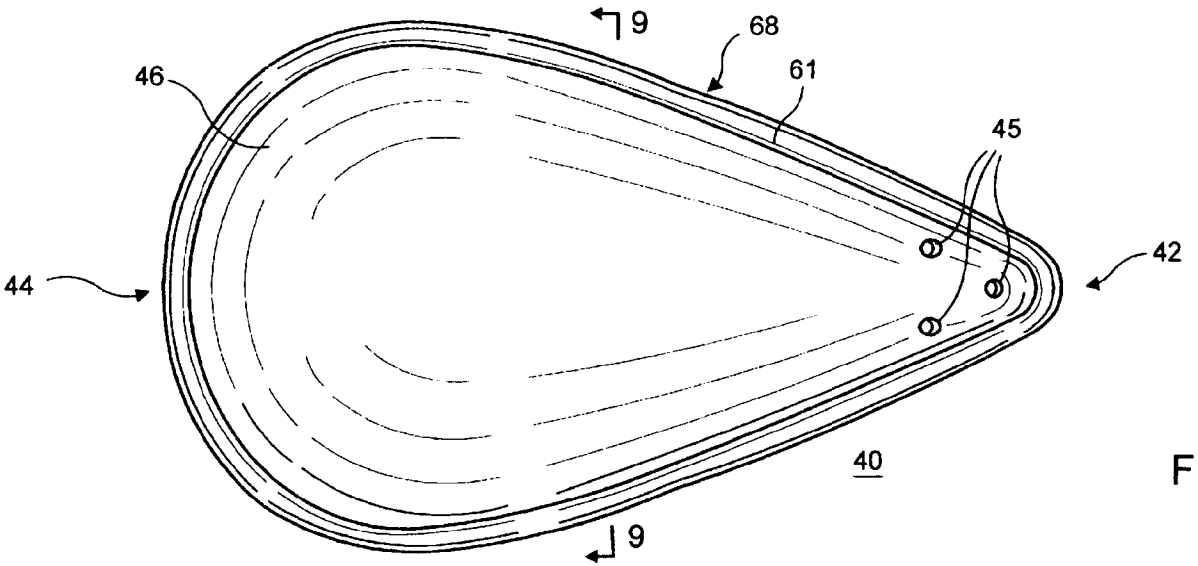
FIG. 8 is a top plan view of the molded body portion depicted in FIG. 7.

Exterior and interior cup surfaces, 16 and 18, are joined at a peripheral edge shown generally at 24. As best illustrated in FIG. 5, peripheral edge 24 actually has a stepped-shaped configuration, forming an inner edge 28 and an outer leading edge 29. Accordingly, in this embodiment of the invention, the exterior cup surface 16 is peripherally bounded at its upper and lower ends by integral, lip portions 20 and 22, respectively, and at its sides by leading edge 29. Similarly, interior cup surface 18 is peripherally bounded by integral lip portions, 20 and 22, and inner edge 28. Preferably, rigid base 10 is further provided with a plurality of apertures 26 for ventilation purposes.

As will be further described herein below, the integral lip portions, 20 and 22, and leading edge 29 provide means for securely integrating the rigid base and resilient body portions of the athletic cup protector of the present invention.

Referring now to FIGS. 7-10, the structure of resilient body 40 will now be described in more detail. Resilient body 40 is preferably constructed from a flexible and resilient elastomer material having a chemical structure compatible with the rigid base member to ensure adequate adhesion thereto. In particular, adhesion at the interfaces should be sufficient to minimize interfacial separation over time under normal cup usage conditions. As will be apparent to those skilled in the art of molding technology, myriad elastomer materials are commercially available for use with the present invention, including, for example, rubber and polyurethane.

Resilient body 40 extends between an upper end 44 and lower end 42 and is comprised of a thin cap-shaped portion, shown generally at 50, and a thickened flange portion, shown generally at 60. As viewed in cross-section, thickened flange portion 60 includes a generally rectangular-shaped portion 62 having a slight lengthwise curve defined by the contour of surface 46, and extends downwardly into an integral crescent-shaped portion 68. The crescent-shaped portion 68 of thickened flange 60 has a cross-sectional area bounded by convex outer surface 61 and concave inner surface 63.

The smooth rounded convex outer surface 61 provides a comfortable, low friction, contact region between the flange and the body of the wearer. This feature of the present invention provides the advantage, vis-a-vis prior art flange designs. This is because this feature reduces body irritation resulting from repeated rubbing of the flange surface against the wearer's body during various body movements including, for example, the repeated bending of a catcher during a baseball game.

Figure 10:
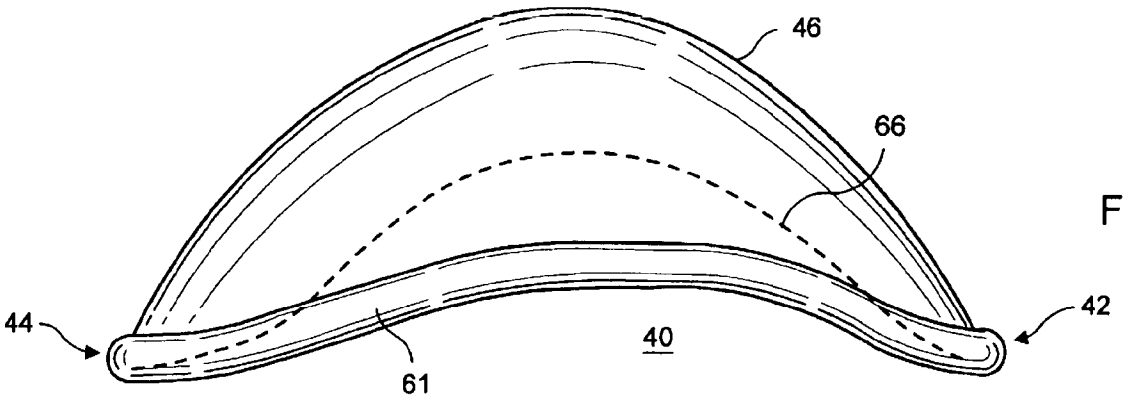
FIG. 10 is a side elevational view of the molded body portion depicted in FIG. 7.

Concave inner surface 63 defines an integral channel 70 which extends around the lower interior of thickened flange 60. Thin cap-shaped portion 50 is bounded by upper surface 46, lower surface 48, and a periphery defined by recessed surface 66 of thickened flange portion 60. As will be described in more detail hereinbelow, during the assembly operation surfaces 64, 65 and 66 of flange portion 62 mate with rigid cup surfaces 28, 27 and 29, respectively. In other words, the surfaces 64, 65 and 66 defining the upper bounds of thickened section 62 correspond to the curved sides 24 of the rigid cup 10. Accordingly, the cross-sectional area of portion 62 varies around the periphery of molded body 40. This variation is best illustrated in FIG. 10, in which thickened flange surface 66 is represented in phantom.

Resilient body 40 can be formed with multiple ventilation apertures 45, so that in the assembled condition of the invention these apertures coincide with the apertures 26 of the rigid cup 10.

Referring now to FIGS. 11-13 and 15, the athletic protector cup of the present invention is illustrated in a fully-constructed, state. It will be apparent to those skilled in the art of athletic protector cups that many conventional means of permanent connection between rigid cup-shaped base member and the flexible resilient body can be utilized. However, the connection between these elements by molding is preferred. It will also be apparent to those skilled in the art of molding that various molding methods incorporating a variety of molding parameters could be employed to achieve the athletic protector cup structure of the present invention. In the preferred embodiment of the present invention, resilient body 40 and rigid cup base 10 are chemically married using an injection molding process. Injection molding of thermoplastic elastomers (TPE) compounds onto engineering thermoplastic resins is well known and is not further described. Specific information relating to TPE injection molding can be found throughout the scientific literature. For example, an article specifically relating to TPE overmolding can be found in the Journal of Injection Molding Technology (March 2000, Vol. 4, No. 1).

Figures 11, 12:
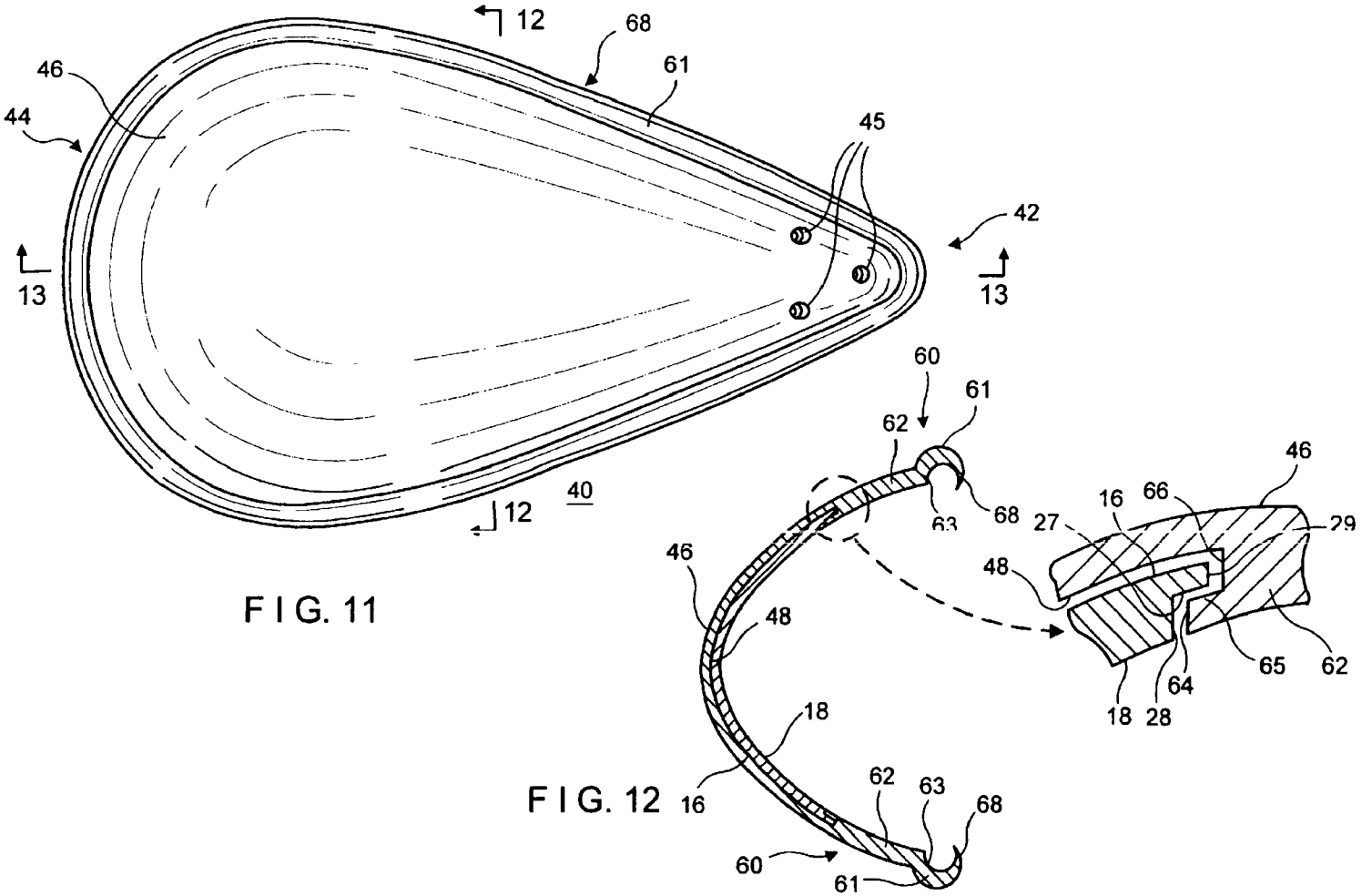
FIG. 11 is a top plan view of a completely constructed athletic protector cup in accordance with the present invention.
FIG. 12 is a cross-sectional view according to section line 12-12 of FIG. 11.
Figure 13:
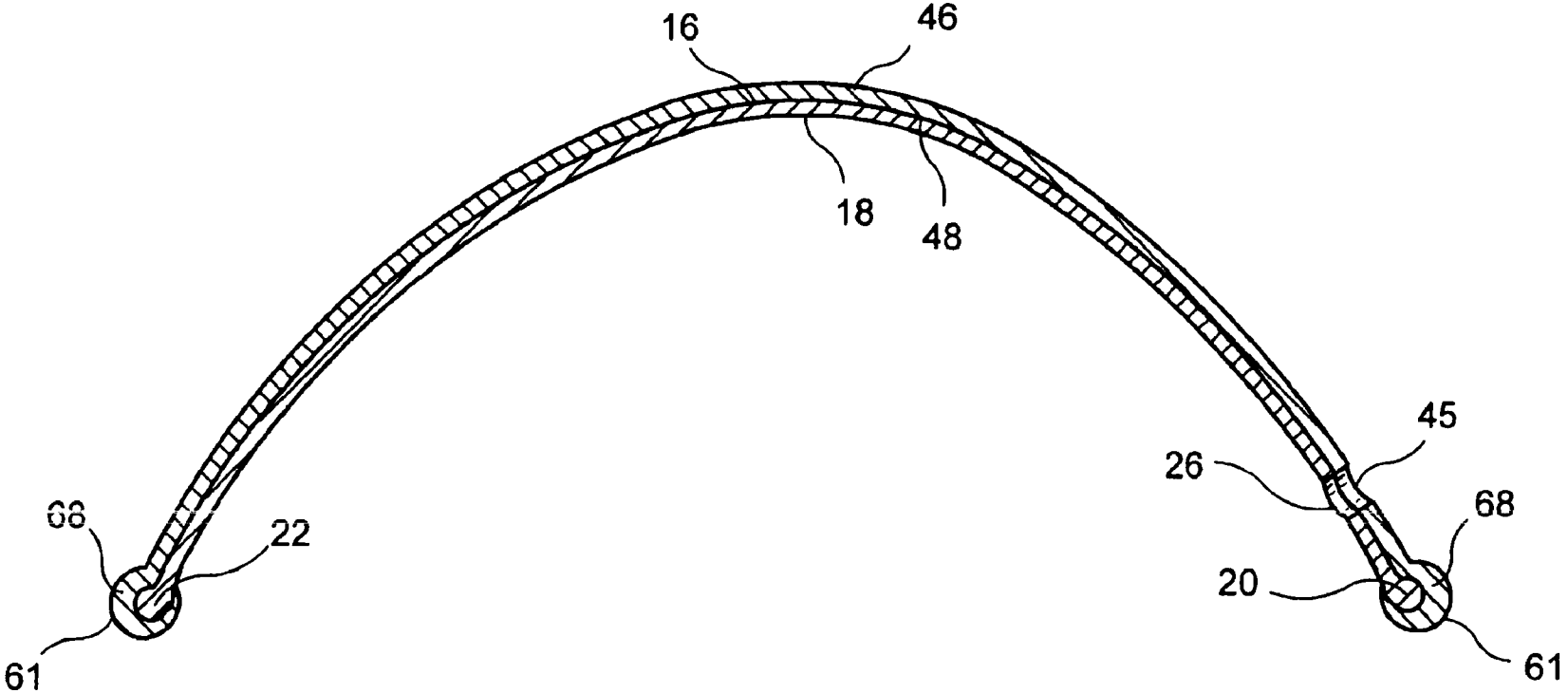
FIG. 13 is a cross-sectional view according to section line 13-13 of FIG. 11.
Figure 14:
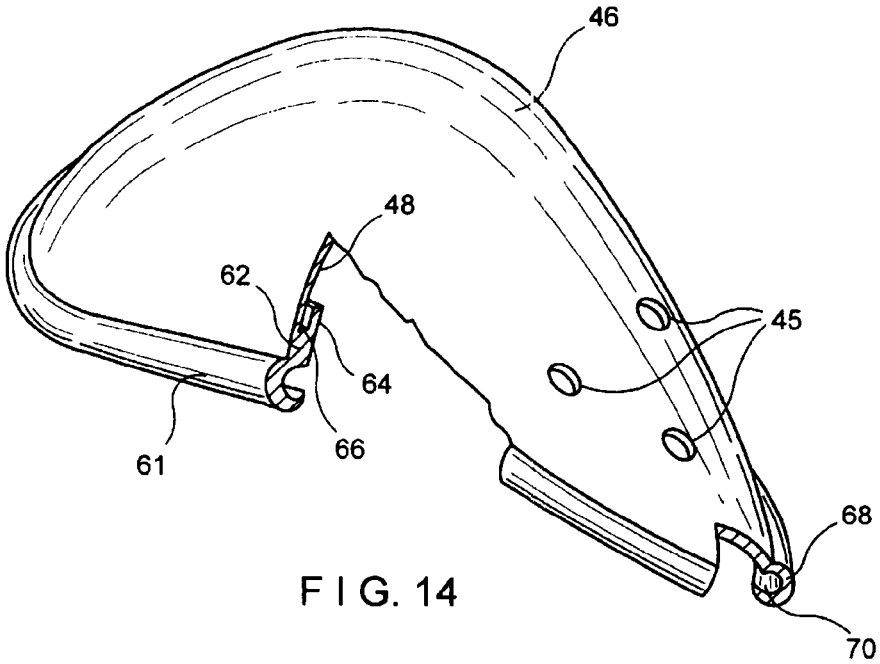
FIG. 14 is a partially fragmented perspective view of the molded body portion of FIG. 7.
Figure 15:
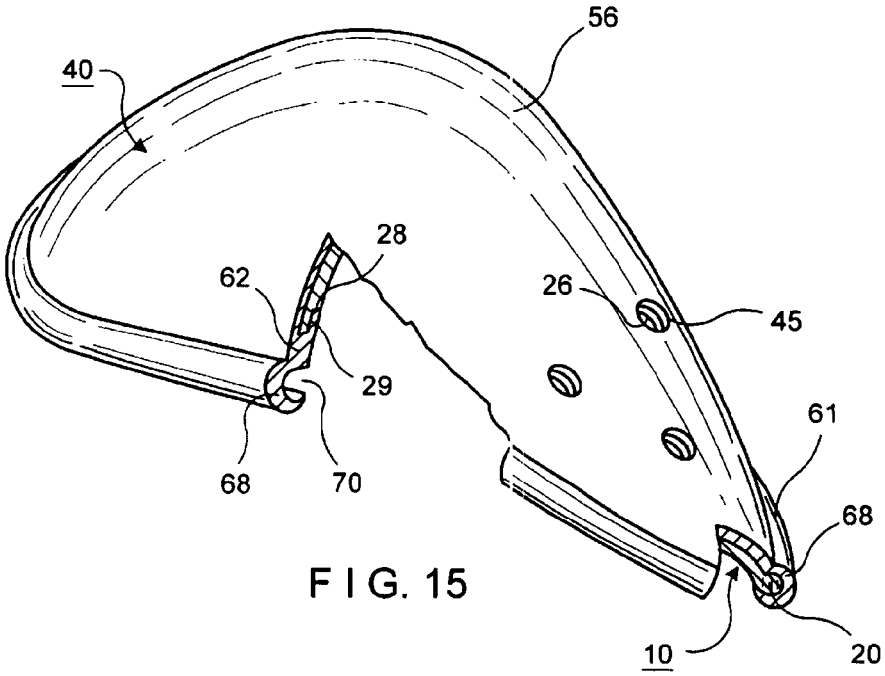
FIG. 15 is a partially fragmented perspective view of a completely assembled athletic protector cup in accordance with a preferred embodiment of the present invention.

Preferably, outer surface 16 of rigid cup 10 is chemically bonded over substantially its entire surface area to interior surface 48 of molded body 40. As best illustrated in FIG. 12, surfaces 27, 28 and 29 of rigid cup 10 are preferably molded to corresponding surfaces 66, 65 and 64 of molded body [10] *40*, thereby forming an interlocking structure for enhancing the stability of rigid cup 10 within molded body 40. As best illustrated in FIG. 13, in this embodiment of the invention, portion 68 of thickened flange 60 completely envelops the integral upper and lower lips 22 and 20 of rigid cup base 10. In a manner similar to the interlocking structure described above, this mating structure further reduces the potential for interfacial separation by maintaining rigid cup 10 and resilient body 40 in a fixed position relative to each other.

The overmolded resilient body structure of the present invention provides numerous significant advantages over the prior art flange structures. For instance, in contrast to known athletic protector cups which provide a resilient body restricted to a peripheral portion of the cup, the resilient elastomer structure of the present invention is molded over the outer surface 16 of the rigid cup to provide an impact resistant barrier. In this manner, the magnitude of a blow to the exterior surface of the protector cup is significantly reduced, or dampened, before being transferred to the rigid plastic inner cup layer. As a result of this improved dampening, the athletic protector cup of the present invention can be constructed using a thinner rigid cup base 10, providing a corresponding weight reduction of approximately 20-30% compared to conventional athletic protector cups.

Figure 16A:
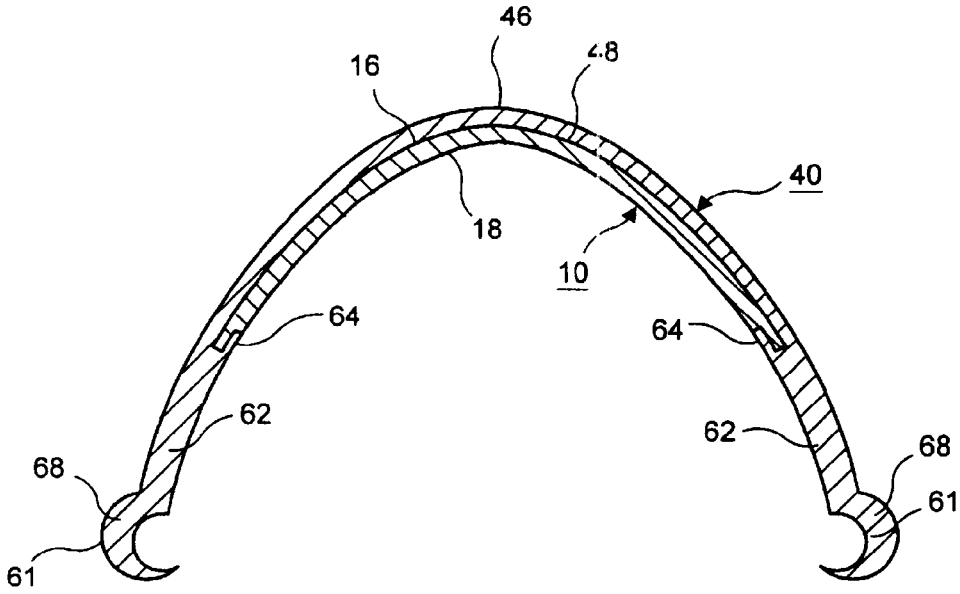
FIG. 16a is identical to the cross-sectional view depicted in FIG. 12 and provided to illustrate the relative horizontal cross-sectional shape of the cup in a non-deflected equilibrium state.
Figure 16B:
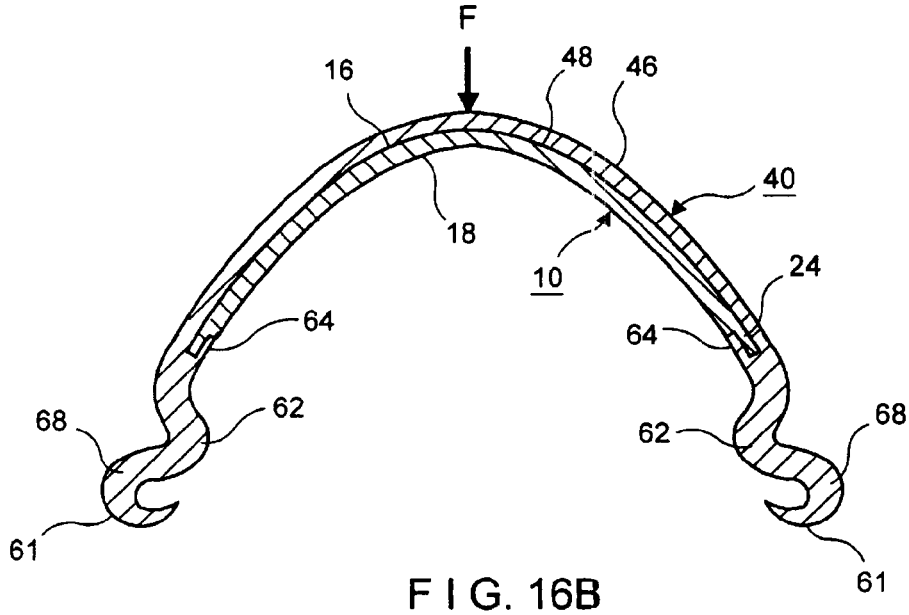
FIG. 16b illustrates the deflection of thickened section 62 of molded body [50] *40* when acted upon by force F.

Further advantages result from the self-collapsing design of the integral flange structure. Referring now to FIGS. 16a and 16b, under the impact of an external force, F, upon outer surface 46, flexible flange portion 62 deflects, or folds, inwardly. At least two significant advantages accrue from this self-collapsing design. First, the inwardly folding flange portion 62 forms a barrier between the rigid perimeter side edges 24 of inner cup 10 and the wearer's body to provide enhanced comfort during the application of a force, F, on the cup. Such force may result from a blow to the cup. Alternatively, such force may result from various bodily movements, such as bending, while wearing the cup. As a consequence of the significant improvements in comfort to the wearer, the athletic protector cup of the present invention lends itself to use by certain athletes, such as soccer players, who commonly play without a protector cup to avoid the discomfort associated with existing cup structures. Second, the inwardly collapsing structure provides enhanced impact resistance in situations where the force results from a blow to the cup, further minimizing the transmission of the force to the wearer's body.

As best illustrated in FIG. 10, in the central region of the athletic protector (commonly engaging the body of the wearer) the rigid peripheral edges of the cup (shown in phantom) are remote from the outer surface 61 of the resilient body portion. Thus, in the assembly of the invention, a substantial portion of the rigid plastic is substituted by a soft plastic of the resilient body, further enhancing comfort to the wearer.

The smooth rounded convex outer surface 61 provides a comfortable, low friction, contact region between the flange and the body of the wearer. Concave inner surface 63 defines an integral channel 70 which extends completely around the lower interior of thickened flange 60.

The resilient body 40 and rigid cup base 10 are fixedly connected. Outer surface 16 of rigid cup 10 is bonded over substantially its entire surface area to interior surface 48 of impact resistant body 40. The surfaces 27, 28 and 29 of rigid cup 10 are attached to corresponding surfaces 65, 64 and 66 of rigid cup 10, thereby forming an interlocking structure. This enables the invention to enhance the stability of rigid cup 10 within body 40.

The flexible end portion 68 of the flexible resilient body envelops the integral upper and lower ends of rigid cup base 10. This mating structure further reduces the potential for interfacial separation by maintaining rigid cup 10 and resilient body 40 in a fixed position relative to each other.

Under the impact of an external force, outer surface of the flexible resilient body [46] *40*, its flexible end flange portion 62 deflects, or folds, inwardly, thereby forming a barrier between the rigid perimeter side edges of cup shaped base member 10 and the wearer's body. This provides enhanced comfort during the application of a force, on the cup. Furthermore, the inwardly collapsing structure enhances impact resistance of the structure when the force of a blow is applied to the cup.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the present invention as described in the claims. For example, resilient body 40 can be further extended over the entire inner surface 18 of rigid cup-shaped base member 10, thereby completely encapsulating the hard cup. The rigid cup-shaped base member can be formed having smooth outer surface and inner surface 18, without lip portions 20 and 22, etc.,.

What is claimed is:

1. An athletic protector, comprising:

a rigid cup-shaped base member having interior and exterior surfaces defined along their peripheries by an outer edge having an anchor formation;

an integral resilient flexible body comprising: a cup-shaped portion, a thickened flanged portion and a transition portion between said cup-shaped portion and said thickened flanged portion;

wherein said cup-shaped portion enveloping substantially the entire exterior surface of said cup-shaped base member, said entire outer edge including the anchor formation is enveloped by said transition portion, and an inner surface of the transition portion and the interior surface of the cup-shaped base member facing a body of a wearer form a continuous smooth internal surface.

2. An athletic protector as recited in claim 1, wherein said integral resilient flexible body is molded over the exterior surface of said rigid cup-shaped base member.

3. An athletic protector as recited in claim 1, wherein said integral resilient flexible body is molded over substantially the entire exterior surface of said rigid cup-shaped base member.

4. An athletic protector as recited in claim 3, further comprising one or more apertures extending through said rigid base member and said resilient body.

5. An athletic protector as recited in claim 3, wherein an upper segment of said rigid cup peripheral edge terminates at an upper integral lip and a lower segment of said peripheral edge terminates at a lower integral lip, said integral resilient flexible body enveloping said upper and lower integral lips.

6. An athletic protector as recited in claim 1, wherein said integral resilient flexible body comprises an elastomer.

7. An athletic protector as recited in claim 1, wherein said resilient flexible body is injection molded to said rigid cup-shaped base.

8. An athletic protector as recited in claim 1, wherein said thickened flanged portion terminates at a rounded end having a generally crescent-shaped cross-sectional geometry, said rounded end having a convex outer surface and a concave inner surface.

9. An athletic protector as recited in claim 1, wherein upon application of a force to an exterior surface of said athletic protector, said thickened flange portion collapses inwardly in such a manner as to form a cushioning barrier between the rigid peripheral edges of said base member and the body of a wearer.

10. An athletic protector as recited in claim 1, further comprising said anchor formation of the outer edge having an outwardly extending solid leading portion; the exterior surface of the cup-shaped base member and an exterior surface of the solid leading portion forming an integral smooth external surface, wherein an interior surface of the solid leading portion has a stepped-shaped configuration.

11. An athletic protector as recited in claim 10, wherein said transition portion is formed with a continuous substantially uninterrupted channel enveloping said solid leading portion and said integral, external smooth surface.

12. An athletic protector, comprising:

a unitary rigid cup-shaped base member having interior and exterior surfaces defined along their peripheries by an outer edge, the edge having upper and lower segments joined by opposite side segments, said upper and lower segments terminating at corresponding upper and lower lips, said opposite side segments having an outer edge with an anchor formation;

an integral resilient body comprising:

a cup-shaped portion, a thickened flanged portion and a transition portion between said cup-shaped portion and said thickened flanged portion;

wherein said cup-shaped portion being molded over so as to envelope substantially the entire exterior surface of said cup-shaped base member, said outer edge including said anchor formation is enveloped by said transition region, and an inner surface of the resilient transition region and the interior surface of the rigid cup-shaped base member facing a body of a wearer form a continuous smooth internal surface.

*13. An athletic protector having an upper, central and lower region and having a first and second sidewall, said protector comprising:*

*a rigid cup-shaped base member having interior and exterior surfaces defined along their peripheries by an outer edge;*

*an integral flexible body comprising: a cup-shaped portion, a flanged portion and a transition portion between said cup shaped portion and said flanged portion;*

*wherein said outer edge is covered by said transition portion; and*

*wherein said first and second sidewalls are substantially comprised of said integral flexible body at said central region.*

*14. The athletic protector as recited in claim 13, wherein said cup-shaped portion substantially covers one of said interior or said exterior surfaces.*

*15. The athletic protector as recited in claim 14, wherein the other of said exterior or said interior surface form a continuous surface with said integral flexible body.*

*16. The athletic protector as recited in claim 13, wherein said upper region is capable of being positioned against the side of a wearer's body while said lower region is capable of being positioned beneath the wearer's body.*

*17. The athletic protector as recited in claim 13, wherein said cup shaped portion substantially covers said cup-shaped base member.*

*18. An athletic protector having upper, central and lower region and a first and second sidewall, said protector comprising:*

*a unitary rigid cup-shaped base member;*

*an integral flexible body comprising: a cup-shaped portion, a flanged portion and a transition portion between said cup shaped portion and said flanged portion;*

*wherein said cup-shaped portion substantially covers said cup-shaped base member; and*

*wherein said first and second sidewalls are substantially comprised of said integral flexible body at said central region.*

*19. The athletic protector as recited in claim 18, wherein one of said interior surface or said exterior surface forms a continuous surface with said integral flexible body.*

*20. An athletic protector having upper, central and lower segments and first and second sidewalls, comprising:*

*a rigid cup-shaped base member having interior and exterior surfaces defined along its periphery by an outer edge having an anchor formation;*

*an integral flexible body comprising: a cup-shaped portion, a thickened flanged portion and a transition portion between said cup shaped portion and said thickened flanged portion;*

*wherein said cup shaped portion substantially covers one of said interior or said exterior surfaces and said anchor*

*formation; and the other of said exterior or said interior surface forms a continuous surface with said integral flexible body; and*

*wherein at least a portion of said first and second sidewalls comprise a portion of said integral flexible body.*

*21. An athletic protector having an upper, central and lower segments and a first and second sidewall, comprising:*

*a unitary rigid cup-shaped base member having interior and exterior surfaces;*

*an integral flexible body comprising: a cup shaped portion, a flanged portion and a transition portion between said cup shaped portion and said flanged portion; and*

*wherein said first and second sidewalls are substantially comprised of said integral flexible body at said central region; and*

*wherein said one of said interior or said exterior surfaces form a continuous surface with said integral flexible body.*

*22. An athletic protector having upper, central and lower regions and having first and second sidewalls, said protector comprising:*

*a rigid cup-shaped base member defined along its periphery by an outer edge, said cup-shaped base member having interior and exterior surfaces; and*

*an integral flexible body comprising a cup-shaped portion, a flanged portion and a transition portion between said cup-shaped portion and said flanged portion;*

*wherein at least a portion of said outer edge is covered by said transition portion; and*

*wherein at least a portion of said first and second sidewalls comprise a portion of said integral flexible body.*

*23. The athletic protector according to claim 22, wherein said flanged portion terminates at a rounded end having a generally crescent-shaped cross-sectional geometry.*

*24. The athletic protector according to claim 22, wherein said cup-shaped portion of said integral flexible body covers at least a portion of said interior surface of said rigid cup-shaped base member.*

*25. The athletic protector according to claim 22, wherein said cup-shaped portion of said integral flexible body covers at least a portion of said exterior surface of said rigid cup-shaped base member.*

*26. The athletic protector according to claim 22, wherein said portion of said integral flexible body comprising at least a portion of the first and second sidewalls comprises said flanged portion.*

*27. An athletic protector having upper, central and lower regions and first and second sidewalls, said protector comprising:*

*a unitary rigid cup-shaped base member; and*

*an integral flexible body comprising a cup-shaped portion, a flanged portion and a transition portion between said cup-shaped portion and said flanged portion;*

*wherein said cup-shaped portion is contiguous with at least a portion of said cup-shaped base member; and*

*wherein at least a portion of said first and second sidewalls comprise a portion of said integral flexible body.*

*28. The athletic protector according to claim 27, wherein the unitary rigid cup-shaped base member has interior and exterior surfaces.*

*29. The athletic protector according to claim 28, wherein said cup-shaped portion of said integral flexible body is contiguous with at least a portion of said interior surface of said unitary rigid cup-shaped base member.*

*30. The athletic protector according to claim 28, wherein said cup-shaped portion of said integral flexible body is contiguous with at least a portion of said exterior surface of said unitary rigid cup-shaped base member.*

*31. The athletic protector according to claim 27, wherein said portion of said integral flexible body comprises said flanged portion.*

*32. The athletic protector according to claim 27, said flanged portion terminates at a rounded end having a generally crescent-shaped cross-sectional geometry.*

*33. An athletic protector having upper, central and lower regions and first and second sidewalls, said protector comprising:*

*a rigid cup-shaped base member defined along its periphery by an outer edge having an anchor formation, said cup-shaped base member having interior and exterior surfaces; and*

*an integral flexible body comprising a cup-shaped portion, a flanged portion and a transition portion between said cup-shaped portion and said flanged portion;*

*wherein said transition portion is contiguous with said anchor formation;*

*wherein said cup-shaped portion is contiguous with at least a portion of one of said interior or exterior surfaces;*

*wherein the other of said exterior or said interior surfaces forms a continuous surface with said integral flexible body; and*

*wherein at least a portion of said first and second sidewalls comprise a portion of said integral flexible body.*

*34. The athletic protector according to claim 33, wherein said portion of the integral flexible body comprising at least a portion of the first and second sidewalls comprises said flanged portion.*

*35. The athletic protector according to claim 33, wherein said flanged portion terminates at a rounded end having a generally crescent-shaped cross-sectional geometry.*

*36. An athletic protector having upper, central and lower segments and first and second sidewalls, comprising:*

*a unitary rigid cup-shaped base member having at least one surface; and*

*an integral flexible body comprising a cup-shaped portion, a flanged portion and a transition portion between said cup-shaped portion and said flanged portion;*

*wherein at least a portion of said first and second sidewalls comprise a portion of said integral flexible body; and*

*wherein said at least one surface of the unitary rigid cup-shaped base member forms a continuous surface with said integral flexible body.*

*37. The athletic protector according to claim 36, wherein the unitary rigid cup-shaped base member has interior and exterior surfaces.*

*38. The athletic protector according to claim 37, wherein the interior surface of the unitary rigid cup-shaped base member forms the continuous surface with said integral flexible body.*

*39. The athletic protector according to claim 37, wherein the exterior surface of the unitary rigid cup-shaped base member forms the continuous surface with said integral flexible body.*

*40. The athletic protector according to claim 36, wherein said flanged portion terminates at a rounded end having a generally crescent-shaped cross-sectional geometry.*

*41. The athletic protector according to claim 36, wherein said portion of said integral flexible member comprising at least a portion of said first and second sidewalls comprises said flanged portion.*

* * * * *

UNITED STATES PATENT AND TRADEMARK OFFICE

CERTIFICATE OF CORRECTION

PATENT NO. : RE43,525 E
APPLICATION NO. : 10/384309
DATED : July 17, 2012
INVENTOR(S) : James J. Landi It is certified that error appears in the above-identified patent and that said Letters Patent is hereby corrected as shown below:

In the Claims

Column 8, line 14, delete the word “an”,
Column 8, line 15, “region” should read --regions--,
Column 8, line 22, “cup shaped” should read --cup-shaped--,
Column 8, line 32, “form” should read --forms--,
Column 8, line 40, “cup shaped” should read --cup-shaped--,
Column 8, line 43, “region” should read --regions--,
Column 8, line 48, “cup shaped” should read --cup-shaped--,
Column 8, line 64, “cup shaped” should read --cup-shaped--,
Column 8, line 66, “cup shaped” should read --cup-shaped--,
Column 9, line 5, “comprise” should read --comprises--,
Column 9, line 6, delete the word “an”,
Column 9, line 10, “cup shaped” should read --cup-shaped--,
Column 9, line 12, “cup shaped” should read --cup-shaped--,
Column 9, line 17, “form” should read --forms--,
Column 9, line 31, “comprise” should read --comprises--,
Column 9, line 57, “comprise” should read --comprises--,
Column 10, line 6, insert the word --wherein-- before the word “said”,
Column 10, line 28, “comprise” should read --comprises--,
Column 10, line 44, “comprise” should read --comprises--.

Signed and Sealed this
Eighteenth Day of March, 2014

Michelle K. Lee

Michelle K. Lee
*Deputy Director of the United States Patent and Trademark Office*